(12) United States Patent
Shvetsov et al.

(10) Patent No.: US 11,589,917 B2
(45) Date of Patent: Feb. 28, 2023

(54) ELECTROSURGICAL DEVICE WITH VACUUM PORT

(71) Applicant: Buffalo Filter, LLC, Lancaster, NY (US)

(72) Inventors: Kyrylo Shvetsov, Depew, NY (US); Michael J. Miller, Depew, NY (US); Gregory Pepe, Lancaster, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 22 days.

(21) Appl. No.: 16/531,410

(22) Filed: Aug. 5, 2019

(65) Prior Publication Data

US 2020/0229861 A1 Jul. 23, 2020

Related U.S. Application Data

(63) Continuation of application No. 15/045,482, filed on Feb. 17, 2016, now Pat. No. 10,405,917, which is a
(Continued)

(51) Int. Cl.
*A61B 18/14* (2006.01)
*A61B 18/00* (2006.01)
*A61B 90/30* (2016.01)

(52) U.S. Cl.
CPC .......... *A61B 18/1477* (2013.01); *A61B 18/14* (2013.01); *A61B 90/30* (2016.02);
(Continued)

(58) Field of Classification Search
CPC ................ A61B 18/14; A61B 18/1477; A61B 2018/00196; A61B 2018/00577; A61B 2018/00589; A61B 2018/00595; A61B 2018/00601; A61B 2018/00607; A61B 2018/00625; A61B 2018/00922;
(Continued)

(56) References Cited

U.S. PATENT DOCUMENTS

| 3,825,004 | A |   | 7/1974  | Durden, III |
| 5,192,267 | A |   | 3/1993  | Shapira et al. |
| 5,234,428 | A |   | 8/1993  | Kaufman |
| 5,269,781 | A |   | 12/1993 | Hewell, III |
| 5,318,565 | A | * | 6/1994  | Kuriloff ............. A61B 18/1402 606/49 |

(Continued)

FOREIGN PATENT DOCUMENTS

GB 2406793 A 4/2005

*Primary Examiner* — Michael F Peffley
(74) *Attorney, Agent, or Firm* — Timothy W. Menasco, Esq.; Harter Secrest & Emery LLP

(57) ABSTRACT

An electrosurgical device having an electrode with a first portion whose exterior is electrically uninsulated, a second portion whose exterior is electrically insulated, and a third portion. An elongated hollow body has an internal cavity, a front end, a rear end, an external surface. An electrical circuit is arranged within the body. The second portion of the electrode is not surrounded by the hollow body. A first button is arranged on the external surface of the body for controlling a current flow at a first level. A vacuum tube is slidably engaged by the body. A vacuum outlet port is arranged near the rear end, and the outlet port, internal cavity, and vacuum inlet are in fluid communication with each other.

18 Claims, 27 Drawing Sheets

Related U.S. Application Data continuation-in-part of application No. 13/021,494, filed on Feb. 4, 2011, now Pat. No. 9,289,261, said application No. 15/045,482 is a continuation-in-part of application No. 13/840,693, filed on Mar. 15, 2013, now Pat. No. 11,357,564.

(60) Provisional application No. 61/301,328, filed on Feb. 4, 2010, provisional application No. 61/318,023, filed on Mar. 26, 2010, provisional application No. 61/645,051, filed on May 9, 2012.

(52) U.S. Cl.
CPC ............... *A61B 2018/00196* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/00625* (2013.01); *A61B 2018/00922* (2013.01); *A61B 2018/00958* (2013.01); *A61B 2018/1412* (2013.01); *A61B 2018/1475* (2013.01); *A61B 2218/005* (2013.01); *A61B 2218/006* (2013.01); *A61B 2218/008* (2013.01)

(58) Field of Classification Search
CPC ............. A61B 2018/00958; A61B 2018/1412; A61B 2018/1475; A61B 2018/005; A61B 2018/006; A61B 2018/008
See application file for complete search history.

(56) References Cited

U.S. PATENT DOCUMENTS

| | | | |
|---|---|---|---|
| 5,413,575 A * | 5/1995 | Haenggi | A61B 18/1402 606/39 |
| 5,709,675 A * | 1/1998 | Williams | A61B 18/00 606/49 |
| 5,730,742 A | 3/1998 | Wojciechowicz | |
| 5,836,944 A * | 11/1998 | Cosmescu | A61B 18/042 604/35 |
| 6,146,353 A * | 11/2000 | Platt, Jr. | A61B 18/00 604/22 |
| 6,635,034 B1 | 10/2003 | Cosmescu | |
| 6,733,495 B1 * | 5/2004 | Bek | A61B 18/00 606/1 |
| 2001/0018586 A1 | 8/2001 | Cosmescu | |
| 2002/0019596 A1 | 2/2002 | Eggers et al. | |
| 2004/0162553 A1 | 8/2004 | Peng et al. | |
| 2005/0060974 A1 | 3/2005 | Palmerton et al. | |
| 2006/0264928 A1 * | 11/2006 | Kornerup | A61B 18/1402 606/45 |
| 2009/0018539 A1 | 1/2009 | Comescu | |
| 2009/0054890 A1 * | 2/2009 | DeCarlo | A61B 90/36 606/34 |
| 2009/0062791 A1 * | 3/2009 | Lee | A61B 18/1402 606/45 |
| 2010/0130972 A1 | 5/2010 | Yambor et al. | |
| 2010/0145333 A1 * | 6/2010 | Dethier | A61B 90/30 606/45 |
| 2011/0190768 A1 | 8/2011 | Shvetsov et al. | |
| 2012/0067212 A1 | 3/2012 | Warren et al. | |
| 2012/0286179 A1 | 11/2012 | Palmerton et al. | |
| 2014/0303449 A1 | 10/2014 | Balog | |

* cited by examiner

ELECTROSURGICAL DEVICE WITH VACUUM PORT

CROSS-REFERENCE TO RELATED APPLICATION

The present application claims the benefit of U.S. patent application Ser. No. 15/045,482 filed on Feb. 17, 2016 and issued as U.S. Pat. No. 10,405,917 on Sep. 10, 2019, which claims the benefit of U.S. patent application Ser. No. 13/021, 494 filed on Feb. 4, 2011 and issued as U.S. Pat. No. 9,289,261 on Mar. 22, 2016, and entitled "Electrosurgical Device with Vacuum Port" which claims the benefit of U.S. Provisional Patent Application No. 61/301,328 filed on Feb. 4, 2010 and U.S. Provisional Patent Application No. 61/318, 023, filed on Mar. 26, 2010, all of which are incorporated herein by reference. The present application also claims the benefit of U.S. patent application Ser. No. 13/840,693 filed on Mar. 15, 2013, and entitled "Electrosurgical Device with Vacuum Port" which claims the benefit of U.S. Provisional Patent Application No. 61/645,051, filed on May 9, 2012, which are incorporated herein by reference.

FIELD OF THE INVENTION

The present invention relates generally to smoke evacuation, and, more specifically, to an electrosurgical device with smoke evacuation during medical procedures.

BACKGROUND

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

With parenthetical reference to the corresponding parts, portions or surfaces of the disclosed embodiment, merely for the purposes of illustration and not by way of limitation, the present invention provides an electrosurgical device comprising: an electrode (26) having a first portion (27) whose exterior is electrically uninsulated, a second portion (28) whose exterior is electrically insulated, and a third portion (30); an elongated hollow body (23) having an internal cavity, a front end, a rear end, an external surface (44), and an electrical circuit arranged within the body, and where the second portion of the electrode is not surrounded by the hollow body. A first button (41) is arranged on the body's external surface (44) for controlling a current flow at a first level. A vacuum tube (29) is slidably engaged by the body and has an inlet (38) generally facing the front end of the body (23). The vacuum tube (29) is arranged to surround the electrode (26). The vacuum tube (29) is also configured to reversibly receive the third portion (30) of the electrode (26) in a separate channel (33) formed at the bottom of the tube (29) such that electrical contact is made between the electrode (26) and a conductor (56). The conductor (56) is connected to the electrical circuit by an electrical connector (59). A vacuum outlet port (24) is arranged near the rear end, and the outlet port, internal cavity, and vacuum inlet are in fluid communication with each other.

The body may be ergonometrically shaped to be received by a user's hand. The inlet to the vacuum tube (29) may be shaped to have a cross section parallel to a user's line of sight towards said electrode (26) when using said device (20). The body (23) may be pencil shaped and may contain friction striations (21). The friction striations may be curved. The electrode (26) may be monopolar, bipolar, or sesquipolar.

The device may have a second button (47) for controlling a current flow at a second level to the electrode (26), and may have a third button to control the vacuum source.

The device may also have: a light source arranged to illuminate an area near the electrode, a battery for providing power to the light source, a button for controlling the illumination light, a swivel joint between the body and the outlet port, and an electrical line may pass through the swivel joint to the electrical circuit.

A filter may be arranged within the internal cavity and the filter may have an RFID tag containing filter information. The vacuum tube inlet may have a substantially rectangular cross section.

In another form, an electrosurgical device (120) comprises: an electrode (126); an elongated hollow body (123) having an internal cavity, a front end, a rear end, an external surface (144), and an electrical circuit arranged within the body (123). The hollow body (123) is shaped to have an ergonometric orientation complementary to a user's hand. A first button (141) controls a current flow at a first level to the electrode (126) and is arranged on the external surface (144). A vacuum tube (129) is slidably engaged by the body (123) and has an inlet shaped to have a cross section parallel to a user's line of sight towards said electrode (126) when using said device (120). The vacuum tube (129) surrounds the electrode (126). The vacuum tube (129) has a blade holder/channel (133) configured to reversibly receive the third portion (130) of the electrode (126) in the center of the vacuum tube (129). A vacuum outlet port is arranged near the rear end of the body (123) and the outlet port, internal cavity, and vacuum inlet are in fluid communication with each other.

The device (120) may be configured to have an electrically insulated portion not surrounded by the body (123) when the electrode (126) is received by the body (123). The body (123) may be pencil shaped and may contain friction striations and the striations may be curved. The electrode (126) may be monopolar, bipolar, or sesquipolar.

The device (120) may have a second button (147) for controlling a current flow at a second level to said electrode (126) or a third button for controlling a vacuum source. The inlet may have a substantially rectangular cross section. The device may also have a light source arranged to illuminate an area near the electrode; a battery for providing power to the light source; a button for controlling the illumination light; and a swivel joint between the body and the outlet port. An electrical line may pass through said swivel joint to the electrical circuit.

The device may contain a filter arranged within the internal cavity and may contain an RFID tag containing filter information.

In another form, an electrosurgical device (220) is provided comprising: an electrode (226); an elongated hollow body (223) having an internal cavity, a front end, a rear end, an external surface, and an electrical circuit arranged within the body (223). The hollow body (223) is shaped to have an ergonometric orientation complementary to a user's hand. A first button (241) controls a current flow at a first level to the electrode (226) and is arranged on the external surface. A vacuum tube (229) is engaged by the body (223) and has an inlet shaped to have a cross section parallel to a user's line of sight towards said electrode (226) when using said device (220). The vacuum tube (229) is configured to reversibly receive the third portion (230) of the electrode (226) in a blade holder/channel (233) mounted in the bottom of the vacuum tube (229). The vacuum tube (229) surrounds the electrode (226). A vacuum outlet port may be arranged near the rear end, and the outlet port, internal cavity, and vacuum inlet are in fluid communication with each other.

The device has means for preventing the vacuum tube from obstructing a user's view of said electrode and means for removing the electrode without electrically contacting the electrode. The means for preventing the vacuum tube from obstructing a user's view may comprise a slidable engagement between the vacuum tube and the body. The means for preventing the vacuum tube from obstructing a user's view may comprise an inlet shaped to have a cross section perpendicular to a user's line of sight towards the electrode when using the device. The means for removing the electrode without electrically contracting the electrode may comprise an insulation coating on the electrode which remains accessible to a user's hand when the electrode is received by the body.

DESCRIPTION OF THE PREFERRED EMBODIMENTS

Figure 1:
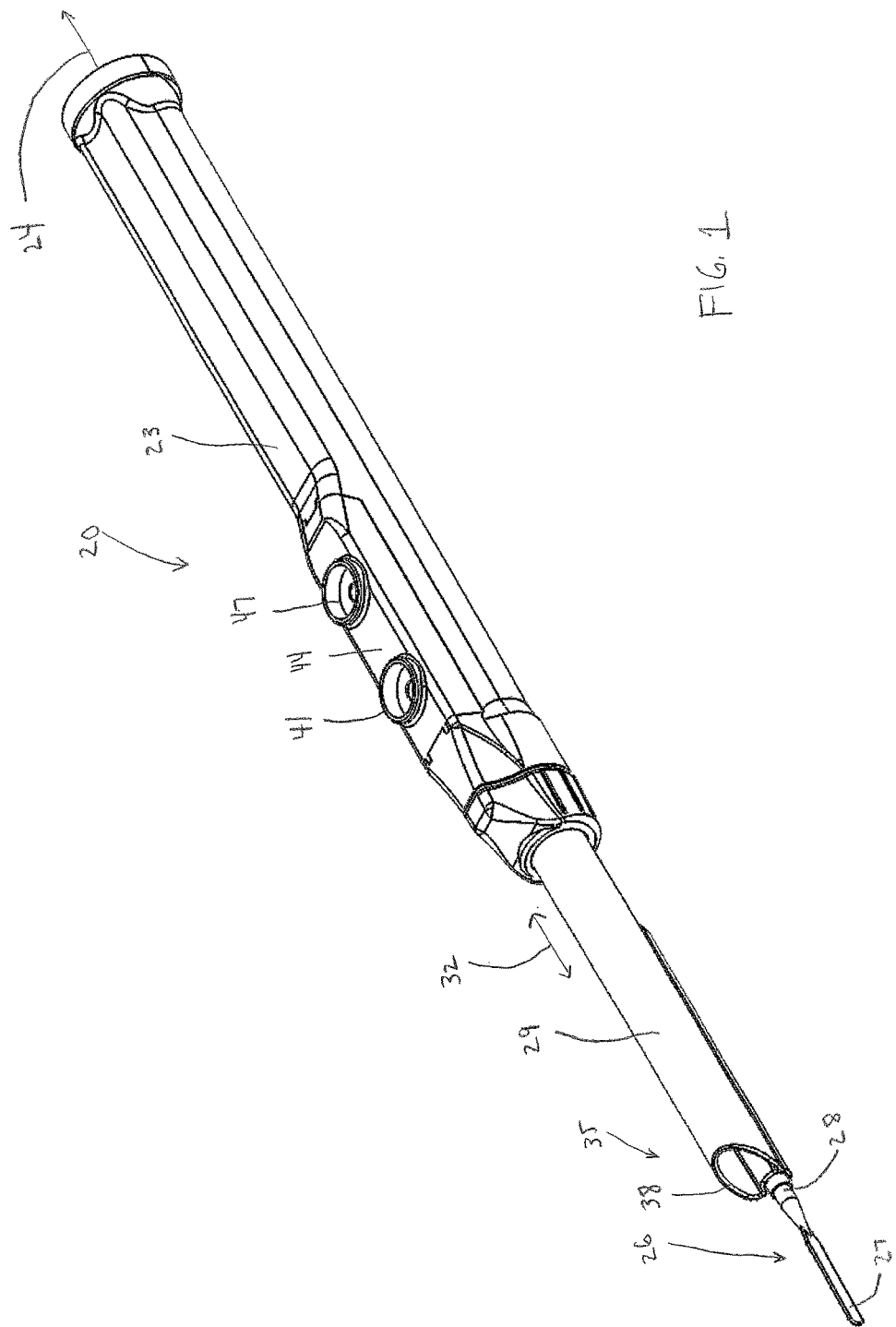
FIG. 1 is a perspective view of a first embodiment of the electrosurgical device of the present invention.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Referring now to the drawings, and more particularly to FIG. 1 thereof, this invention provides an electrosurgical pen 20 having a body 23. The body 23 may be ergonomically shaped to be received by a user's hand. The body 23 may be pencil shaped and may have a longitudinal axis 24. On the left side of the figure, an electrode 26 is removably attached to a vacuum tube 29. The electrode 26 may have a uninsulated end portion 27, insulated portion 28, and a mounting portion 30. The vacuum tube 29 is mounted on the body 23 and may extend telescopically from the body 23 in an axial direction 32. The distal end 35 of the vacuum tube 29 comprises an inlet 38 shaped to have a cross section parallel to a user's line of sight towards said electrode 26 when using the pen 20.

The pen 20 may be provided with a first button 41 arranged on the external surface 44 of the body 23. The first button 41 may control the current flow to the device at a first level. The pen 20 may have a second button 47 for controlling a current flow at a second level to the electrode 26. Additional buttons may be added for controlling the vacuum source, a light source or the like.

Figure 2:
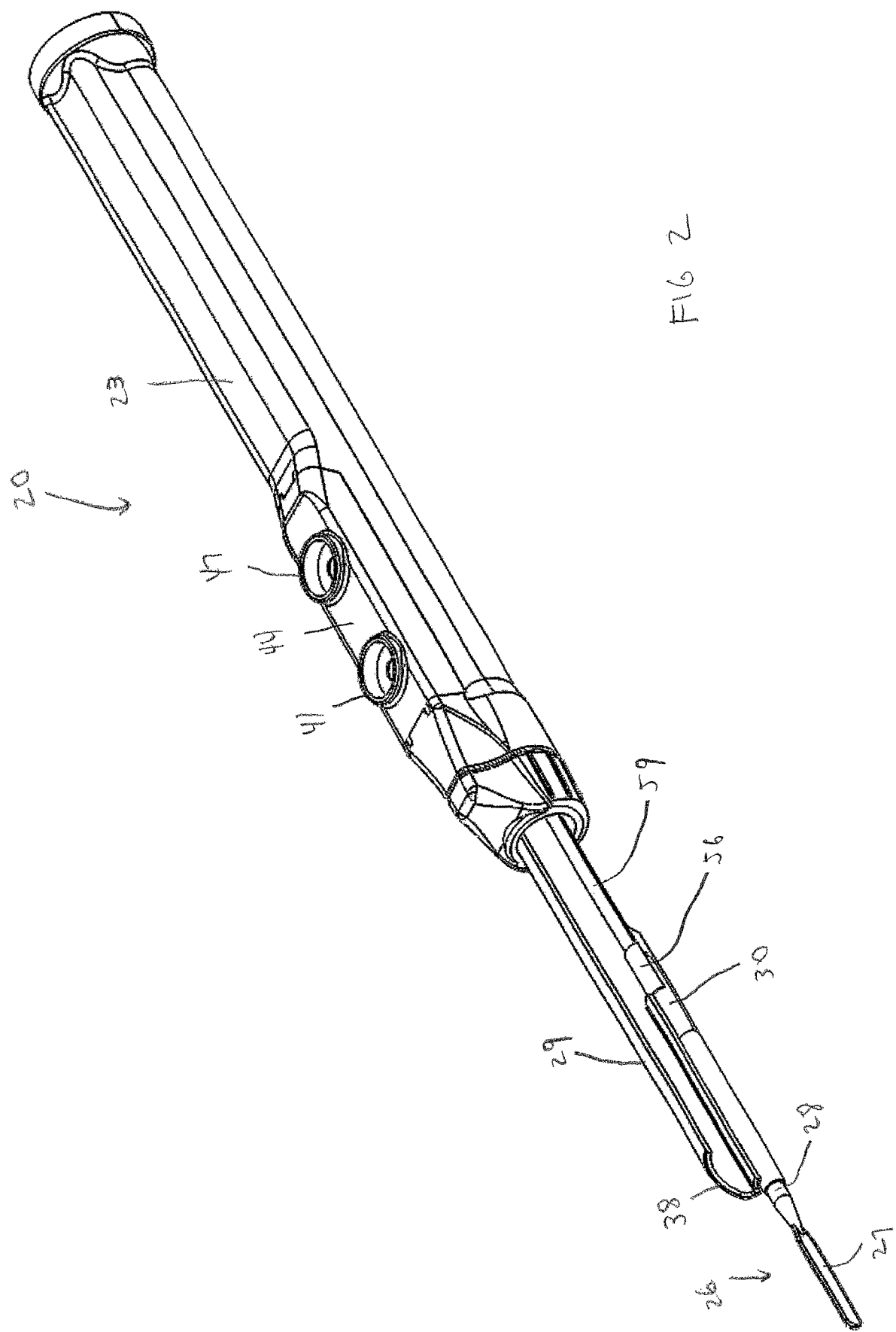
FIG. 2 is a partial cutaway perspective view of the device of FIG. 1.

Turning to FIG. 2, a portion of the vacuum tube 29 has been removed for clarity. The tube 29 has a set of opposed walls 50, 53 (FIG. 4) forming a channel/blade holder 33 at the bottom of the tube 29 for receiving the electrode 26. At the end of the channel/blade holder 33, there is a conductor 56 that is electrically connected by an electrical connector 59 to a circuit (not shown) inside the body 23 that provides current to the electrode 26 for operation of the device 20. The first and second buttons 41, 47 are electrically associated with the electric circuit inside the body 23 to provide different levels of current to flow to the electrode 26 depending on whether the device 20 is being used for cutting or coagulating. The end 27 of the electrode 26 is uninsulated for use as an electric blade for cutting and cauterizing during medical procedures. A midportion 28 of the electrode is insulated so that the user can remove the electrode 26 from the device. A base portion 30 of the electrode 26 is designed to make contact with the conductor 56 at the end of the channel 33 in the tube 29 and to removably attach the electrode 26 to the device 20 inside the tube 29.

Figure 3:
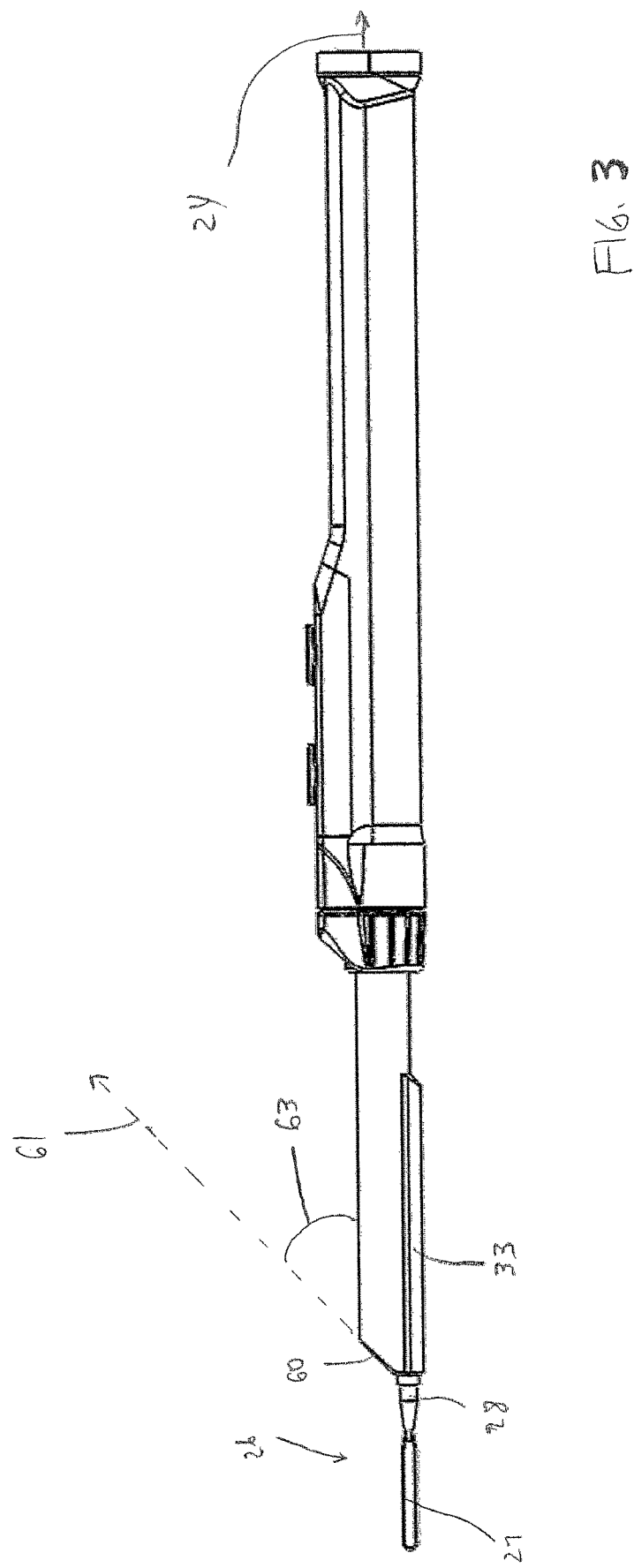
FIG. 3 is a side elevational view of the device of FIG. 1.

In FIG. 3, the placement of the blade holder/channel 33 at the bottom of the tube 29 is shown. The electrode 26 slides into the blade holder 33 and is held in place by a frictional fit inside the channel. As shown the end of the tube 29 is shaped to have a cross section 60 disposed along an axis 61 at an acute angle 63 relative to the longitudinal axis 24 of the device 20 such that the angle of the chamfer at the end of the tube 29 is parallel to a user's line of sight toward the electrode 26 when using the pen 20. The vacuum tube 29 may be telescopically or fixedly attached to the body 23 of the device 20 in the position shown. Electrodes 26 having different lengths, widths, etc. may be switched in and out of the blade holder 33 in the device 20 to accommodate different patients and different procedures.

Figure 4:
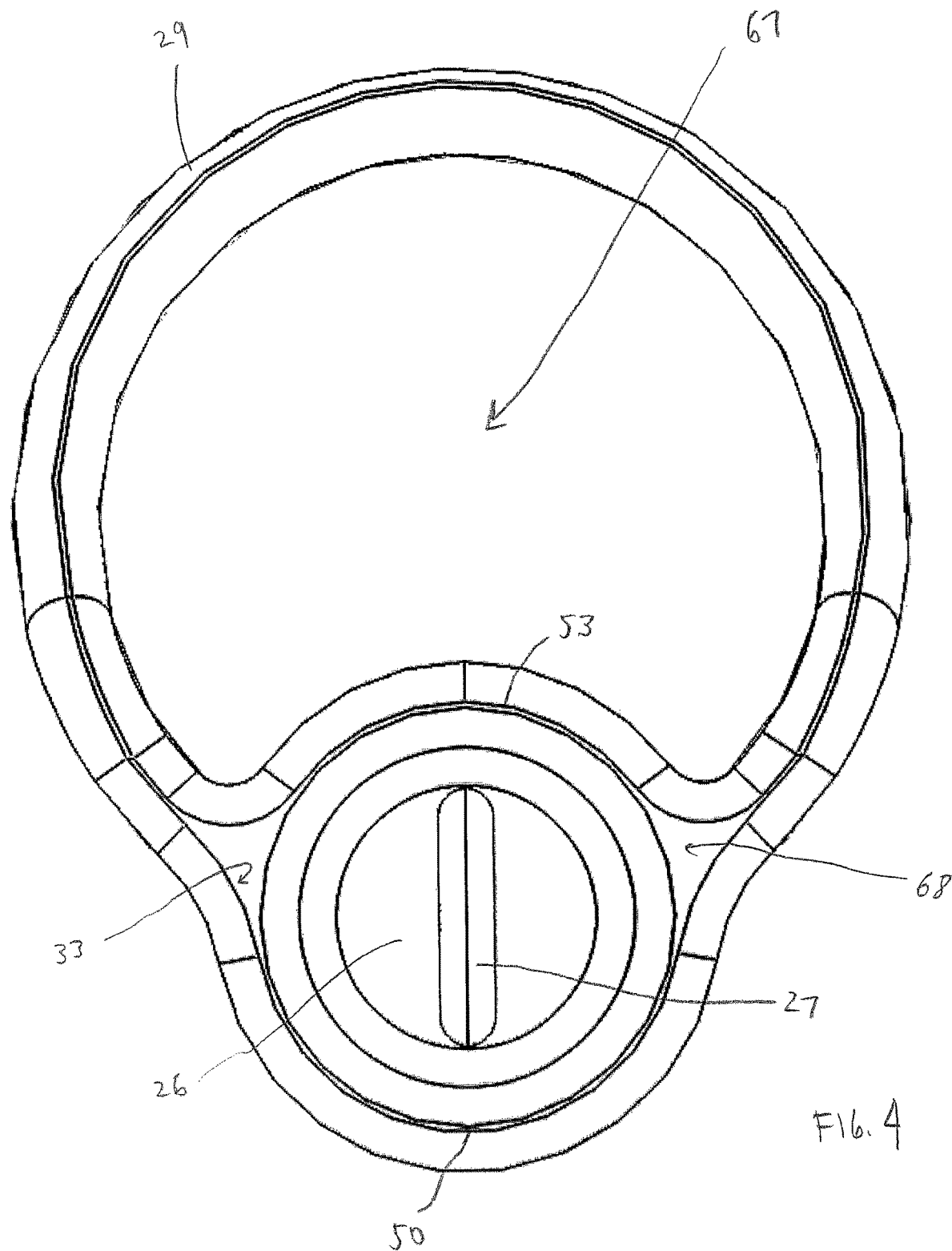
FIG. 4 is a front elevational view of the tube and electrode of the device of FIG. 1.

Turning to FIG. 4, a separate channel 33 may be formed in the tube 29 for receiving the electrode 26. The surgical smoke is evacuated through the passageway 67 formed at the top of the tube 29. An opening 68 provides entry into the channel 33 formed between curved walls 50 and 53 in the bottom portion of the tube 29. The channel 33 is sized to receive the electrode 26. The opening 68 leads to the channel 33 which extends axially along the length of the tube 29. At the end of the channel 33, the base 30 of the electrode 26 contacts the conductor 56 to establish electrical contact between the electrode 26 and the electrical circuit in the device 20. The electrical circuit in the device 20 provides current to the electrode 26. The current may be provided at different levels depending on the application. For cutting, a higher current level is required, whereas, coagulation requires less current.

Figure 5:
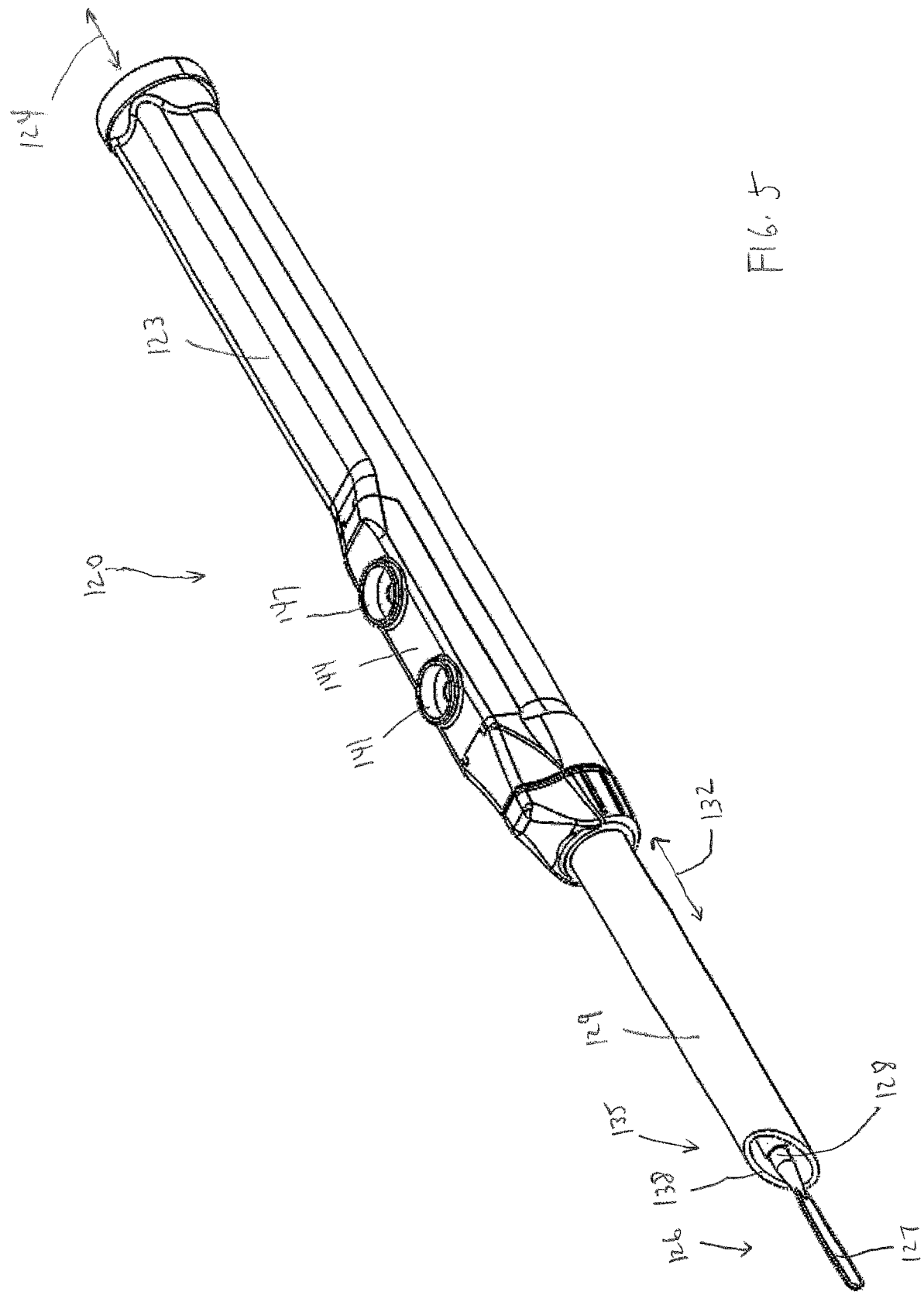
FIG. 5 is a perspective view of an alternate embodiment of the electrosurgical device of the present invention.

In FIG. 5, an alternate embodiment of the electrosurgical device is shown. In contrast to the embodiment of FIGS. 1-4, an electrode 126 is held in the center of a tube 129 by a blade holder 133 (FIG. 6) disposed inside the tube 129. The body 123 may be ergonomically shaped to be received by a user's hand. The body 123 may be pencil shaped and may have a longitudinal axis 124. On the left side of the figure, an electrode 126 is removably attached to a vacuum tube 129. The electrode 126 may have a uninsulated end portion 127, insulated portion 128, and a mounting portion 130. The vacuum tube 129 is telescopically mounted on the body 123 and extends from the body in an axial direction 132. The distal end 135 of the vacuum tube 129 comprises an inlet 138 shaped to have a cross section parallel to a user's line of sight toward the electrode 126 when using the pen 120.

The pen 120 may be provided with a first button 141 arranged on an external surface 144 of the body 123. The first button 141 may control the current flow to the device 120 at a first level. The pen 120 may have a second button 147 for controlling a current flow at a second level to the electrode 126. Additional buttons may be added for controlling the vacuum source, a light source or the like.

Figure 6:
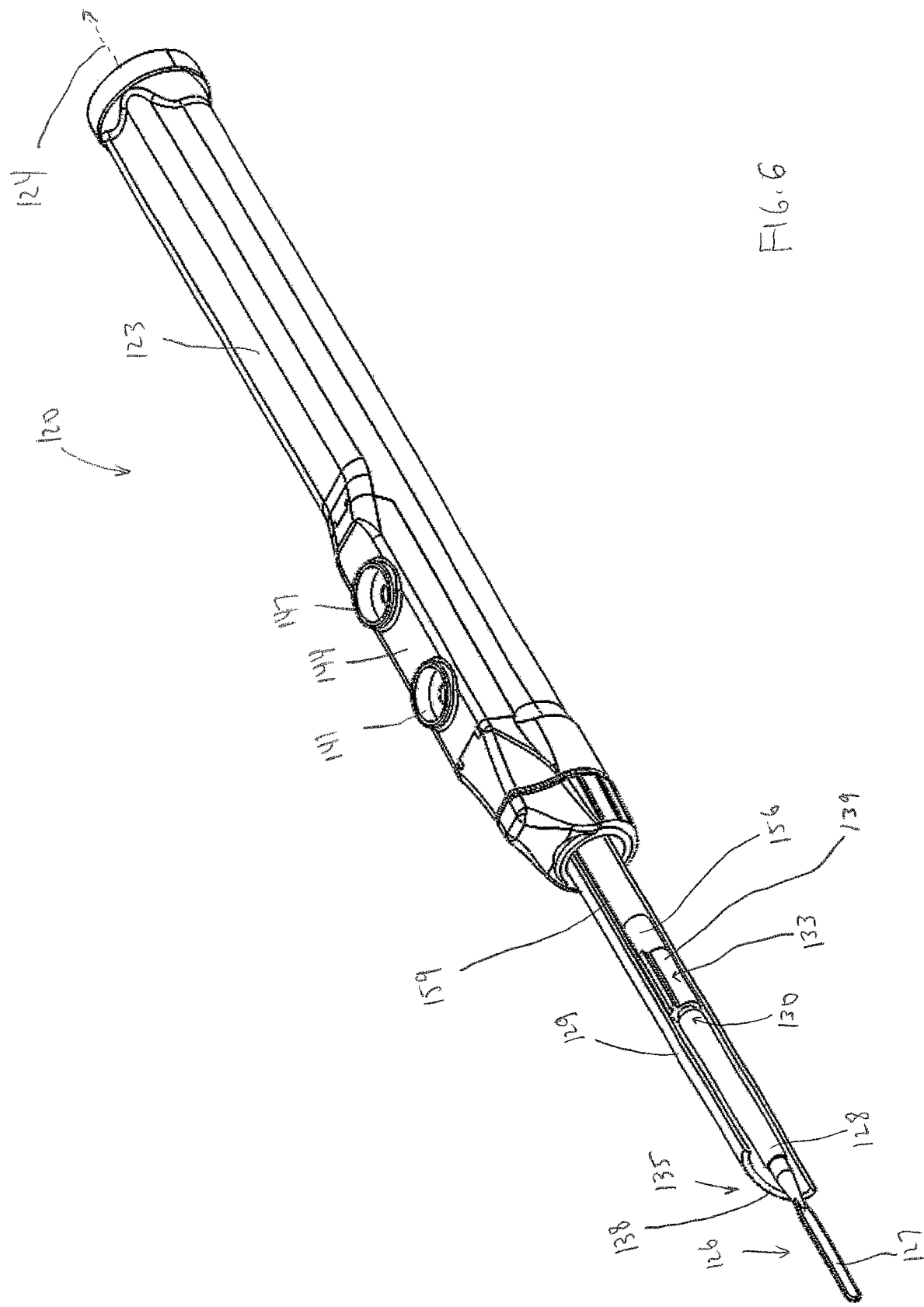
FIG. 6 is a partial cutaway perspective view of the electrosurgical device of FIG. 5.

Turning to FIG. 6, a portion of the vacuum tube 129 has been removed for clarity. The tube 129 has a channel/blade holder 133 defined therein for receiving the electrode. At the end of the channel 133, there is a conductor 156 that is electrically connected by an electrical connector 159 to a circuit inside the body 123 that provides current to the electrode 126 for operation of the device 120. The first and second buttons 141 and 147 are electrically associated with the electric circuit inside the body 123 to provide different levels of current to flow to the electrode 126 depending on whether the device 120 is being used for cutting or coagulating. The end 127 of the electrode 126 is uninsulated for use as an electric blade for cutting and cauterizing during medical procedures. A midportion 128 of the electrode 126 is insulated so that the user can remove the electrode 126 from the device 120. A base portion 130 of the electrode 126 is designed to make contact with the conductor 156 at the end of the channel 133 in the tube 129 and to removably attach to the device 120 inside the tube 129. The blade holder 133 is mounted inside the vacuum tube 129. The blade holder 133 has a longitudinal channel formed therein for receiving the electrode 126. The body 139 of the blade holder 133 is round and fits inside the center of the vacuum tube 129. The blade holder 133 has a pair of ribs 180, 183 (FIG. 8) extending from one side that engage with the inside of the tube 129. The blade holder 133 provides for the flow of surgical smoke around the blade holder 133 and the ribs 180, 183 through the tube 129.

Figure 7:
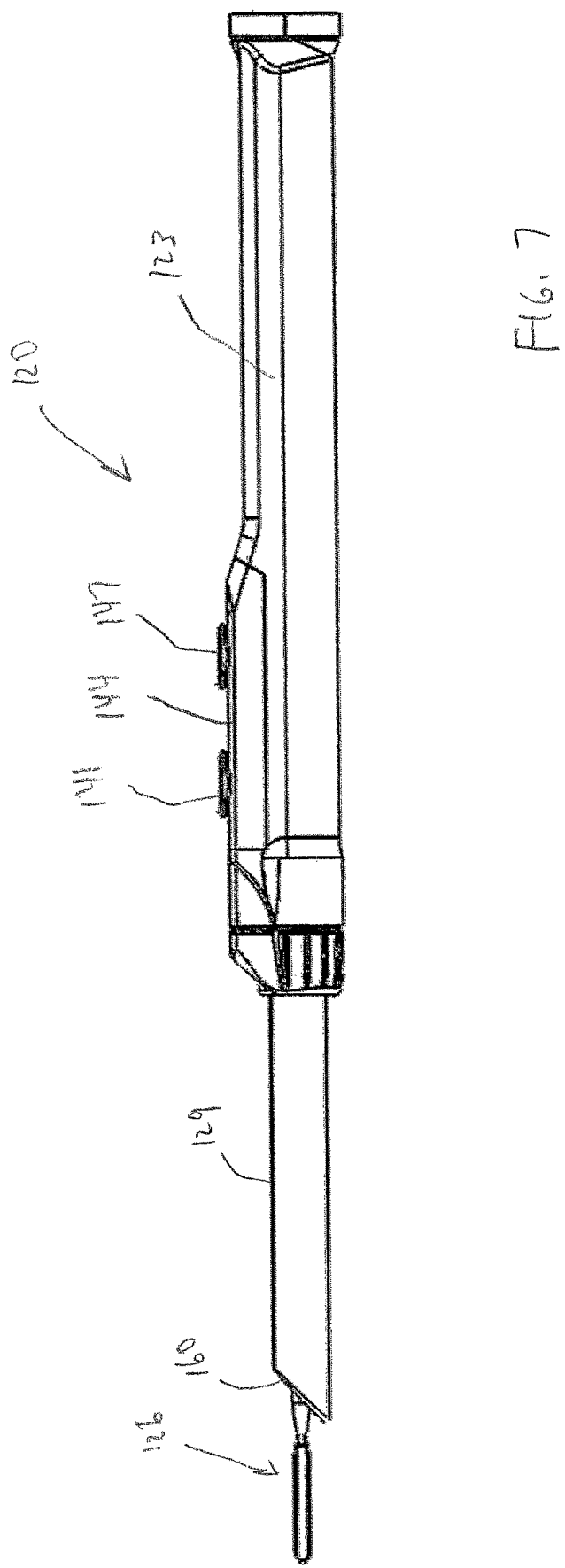
FIG. 7 is a side elevational view of the device of FIG. 5.

In FIG. 7, the orientation of the blade holder 133 in the center of the tube 129 is best shown based on the position of the electrode 126. The electrode 126 slides into the blade holder 133 and is held in place by a frictional fit inside the channel. As shown the end 160 of the tube 129 is shaped to have a cross section parallel to a user's line of sight toward the electrode 126 when using the pen 120. The vacuum tube 129 may be telescopically attached to the body 123 as will be evident to those of ordinary skill in the art based on this disclosure. The vacuum tube 129 may also be fixedly attached to the body 123. Electrodes 126 having different lengths, widths, etc. may be switched in and out of the blade holder 133 in the device to accommodate different patients and different procedures.

Figure 8:
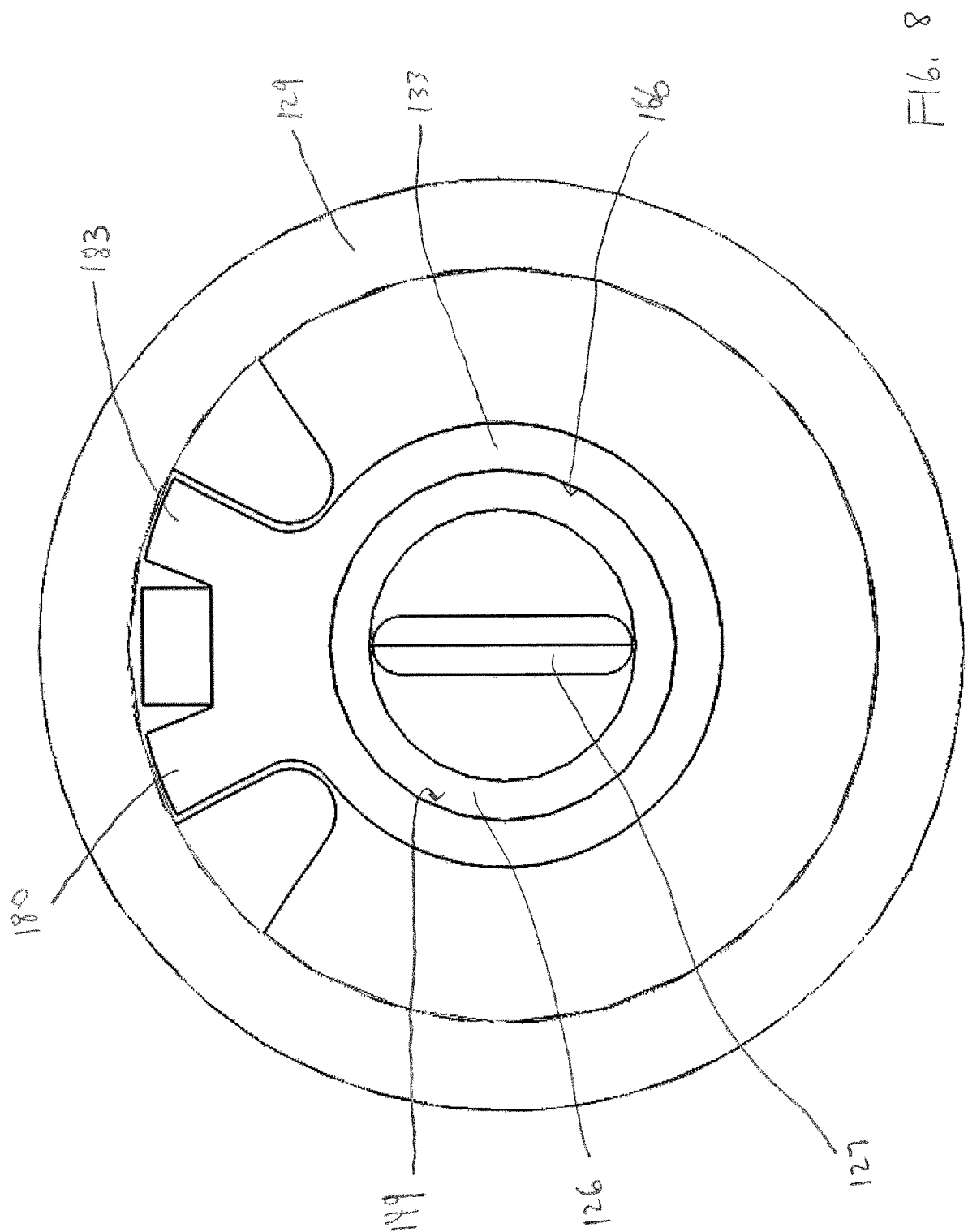
FIG. 8 is a front elevational view of the tube and electrode of the device of FIG. 5.

Turning to FIG. 8, a separate channel 149 is formed in the blade holder 133 for receiving the electrode 126. The surgical smoke is evacuated through the passageway formed around the blade holder 133 and its ribs 180, 183. The opening formed in the blade holder 133 mounted in the tube 129 is sized to interchangeably receive one or more electrodes 126. The opening leads to a channel 166 extending axially along the length of the tube 129. At the end of the channel 166, the base 130 of the electrode 126 contacts a conductor 156 to establish electrical contact between the electrode 126 and the electrical circuit (not shown) in the device 120. The electrical circuit in the device provides current to the electrode 126. The current may be provided at different levels depending on the application. For cutting, a higher current level is required, whereas, coagulation requires less current.

Figure 9:
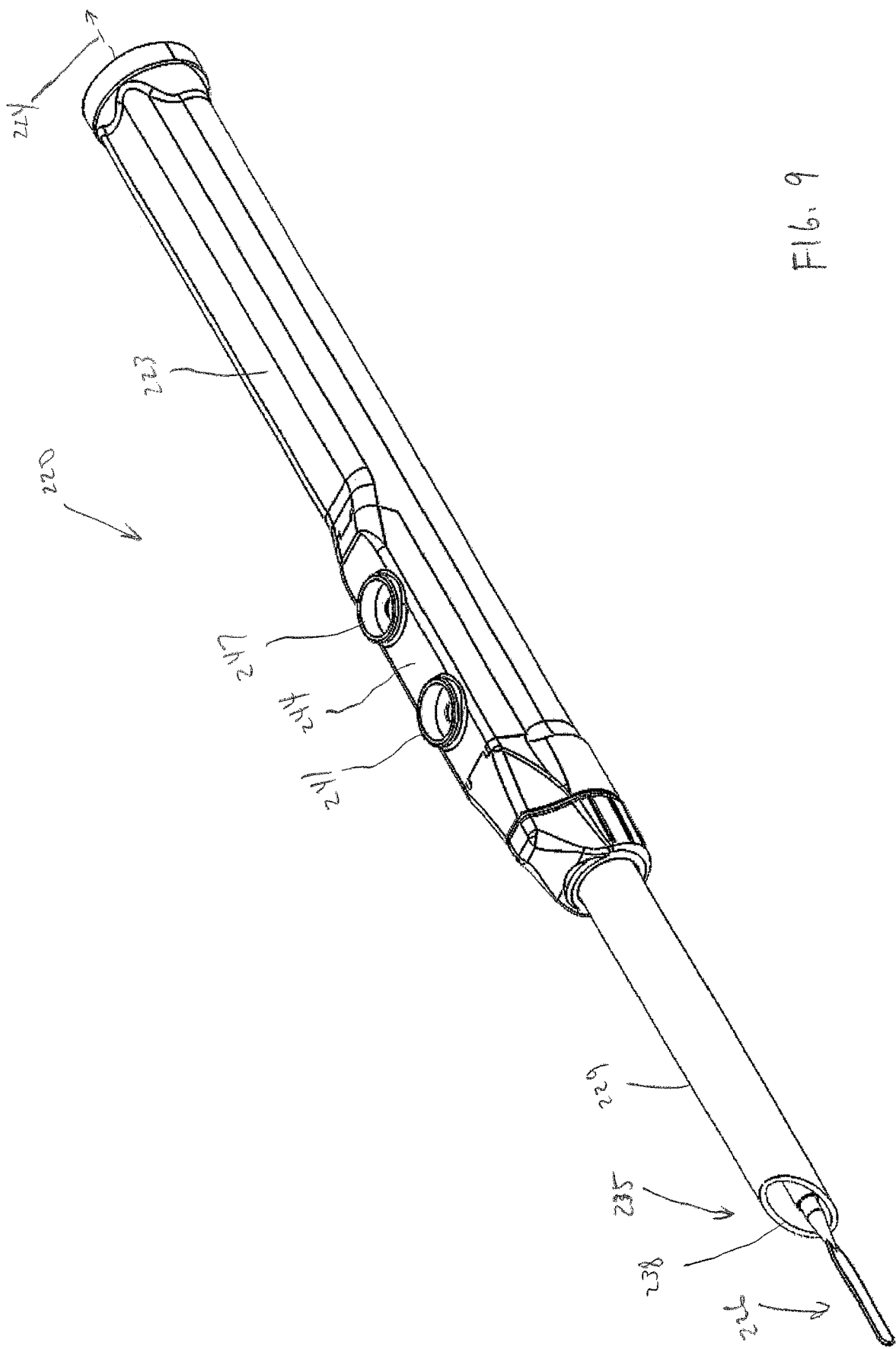
FIG. 9 is a perspective view of another alternate embodiment of the electrosurgical device of the present invention.

In FIG. 9, an alternate embodiment of the electrosurgical device is shown. A blade holder 233 (FIG. 10) is disposed inside the tube 229 but the electrode 226 is positioned at a bottom portion of the tube 229. The body 223 may be ergonomically shaped to be received by a user's hand. The body 223 may be pencil shaped and may have a longitudinal axis 224. On the left side of the figure, an electrode 226 is removably attached to a vacuum tube 229. The electrode 226 may have a uninsulated end portion 227, insulated portion 228, and a mounting portion 230. The vacuum tube 229 is mounted on the body 223 and extends from the body in an axial direction 232. The distal end 235 of the vacuum tube 229 comprises an inlet 238 shaped to have a cross section parallel to a user's line of sight toward the electrode 226 when using the pen 220.

The pen 220 may be provided with a first button 241 arranged on the external surface 244 of the body 223. The first button 241 may control the current flow to the device at a first level. The pen 220 may have a second button 247 for controlling a current flow at a second level to the electrode 226. Additional buttons may be added for controlling the vacuum source, a light source or the like.

Figure 10:
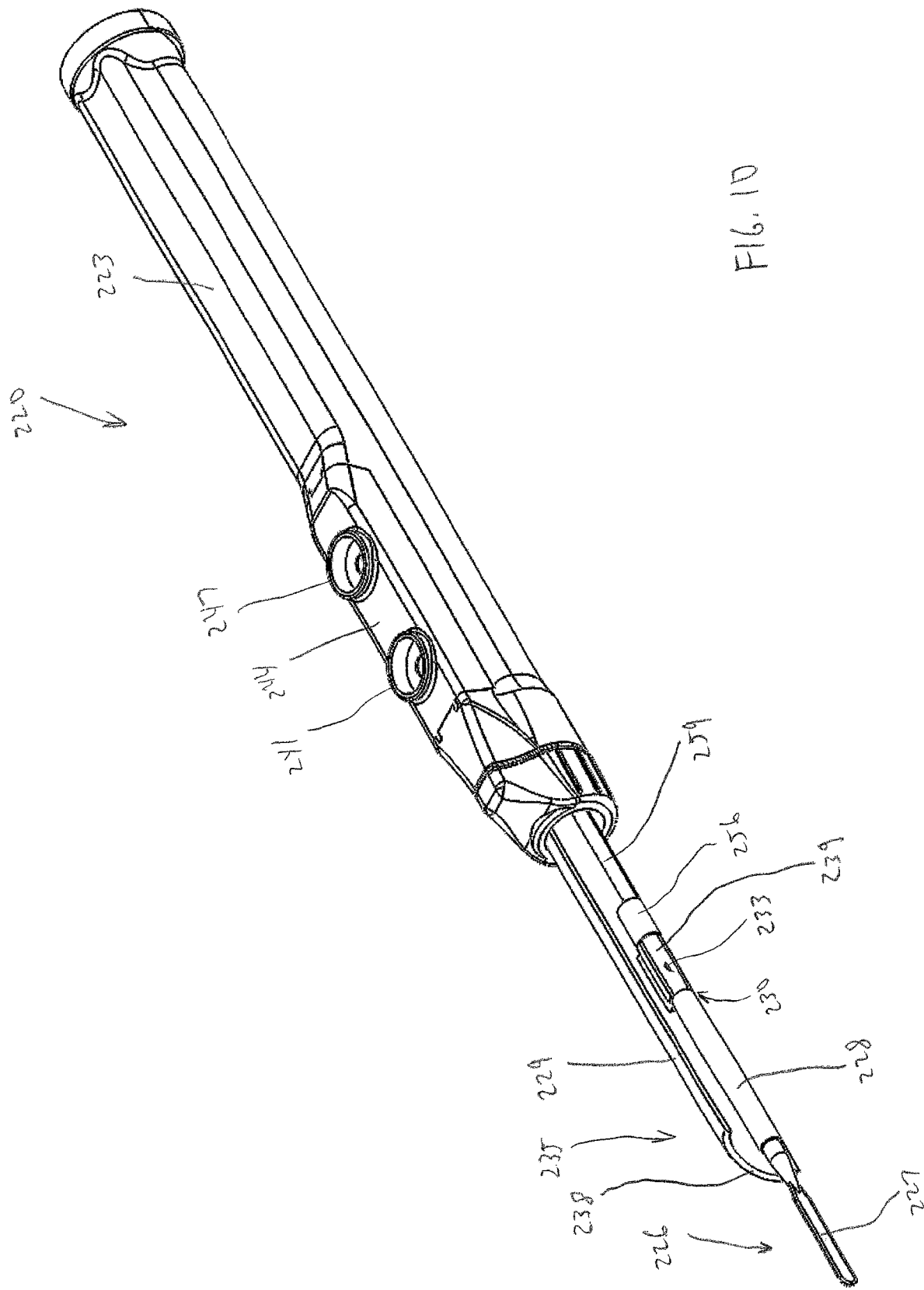
FIG. 10 is a partial cutaway perspective view of the electrosurgical device of FIG. 9.

Turning to FIG. 10, a portion of the vacuum tube 229 has been removed for clarity. The tube 229 has a channel/blade holder 233 defined therein for receiving the electrode 226. At the end of the channel, there is a conductor 256 that is electrically connected by an electrical connector 259 to a circuit inside the body 223 that provides current to the electrode 226 for operation of the device 220. The first and second buttons 241, 247 are electrically associated with the electric circuit inside the body 223 to provide different levels of current to flow to the electrode 226 depending on whether the device 220 is being used for cutting or coagulating. The end 227 of the electrode 226 is uninsulated for use as an electric blade for cutting and cauterizing during medical procedures. A midportion 228 of the electrode 226 is insulated so that the user can remove the electrode 226 from the device 220. A base portion 230 of the electrode 226 is designed to make contact with the conductor 256 at the end of the channel 233 in the tube 229 and to removably attach to the device 220 inside the tube 229. The blade holder 233 is mounted inside and toward the bottom of the vacuum tube 229. The blade holder 233 has a longitudinal opening for receiving the electrode 226. The body 239 of the blade holder 233 is round and fits inside the vacuum tube 229 toward the bottom of the tube 229. The blade holder 233 is attached to the inside of the tube 229. The blade holder 233 provides for the flow of surgical smoke around the blade holder 233 through the tube 229.

Figure 11:
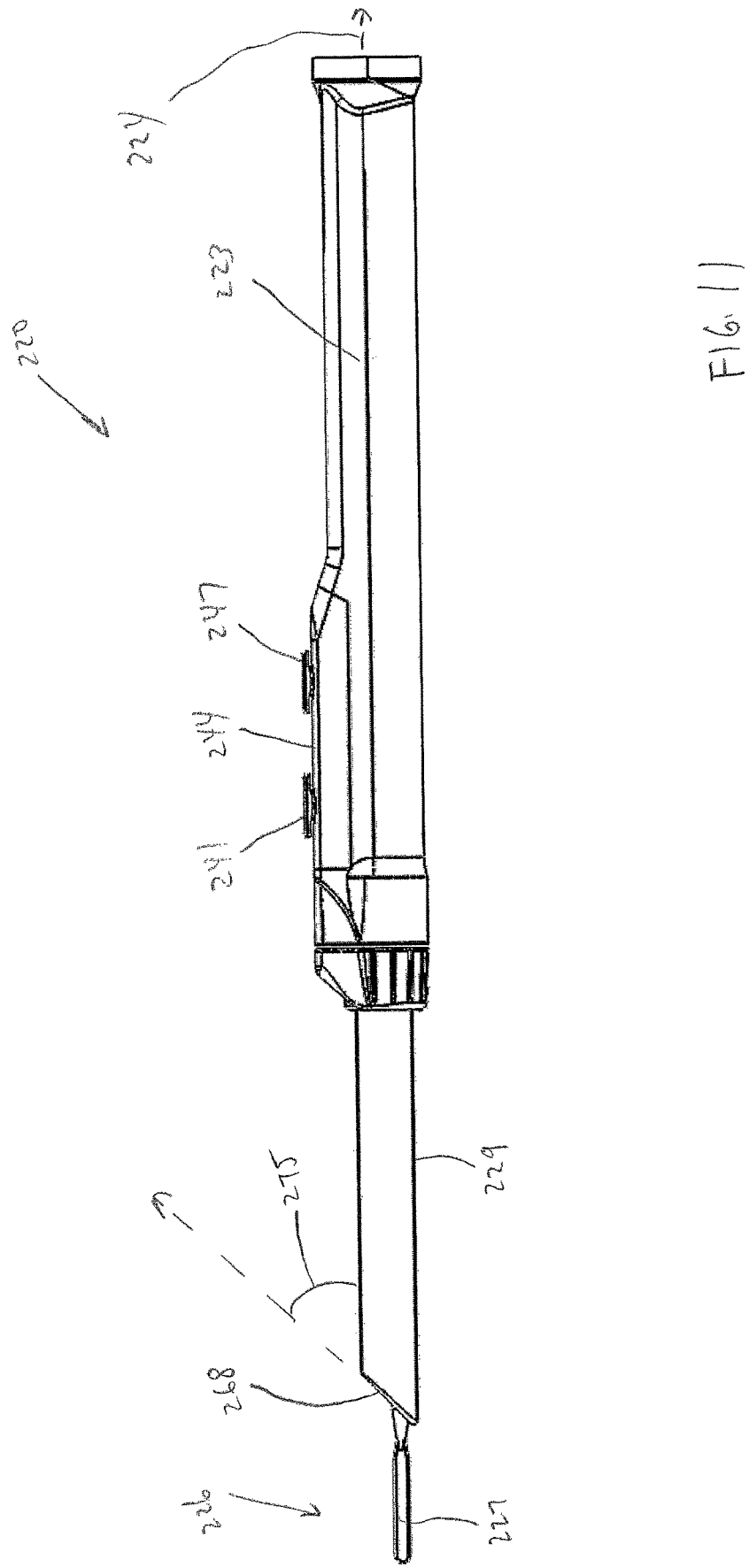
FIG. 11 is a side elevational view of the device of FIG. 9.

In FIG. 11, the placement of the blade holder 233 toward the bottom of the tube 229 is best shown based on the position of the electrode 226 relative to the tube 229. The electrode 226 slides into the blade holder 233 and is held in place by a frictional fit inside the channel. As shown the end of the tube 229 is shaped to have a cross section parallel to a user's line of sight toward the electrode 226 when using the pen 220. The end 268 of tube 229 is cut at an acute angle 275 relative to the longitudinal axis 224 of device 220. The vacuum tube 229 may be telescopically attached to the body 223 of the device 220 in the position shown or may be fixedly attached as will be evident to those of ordinary skill in the art based on this disclosure. Electrodes 226 having different lengths, widths, etc. may be switched in and out of the blade holder in the device to accommodate different patients and different procedures.

Figure 12:
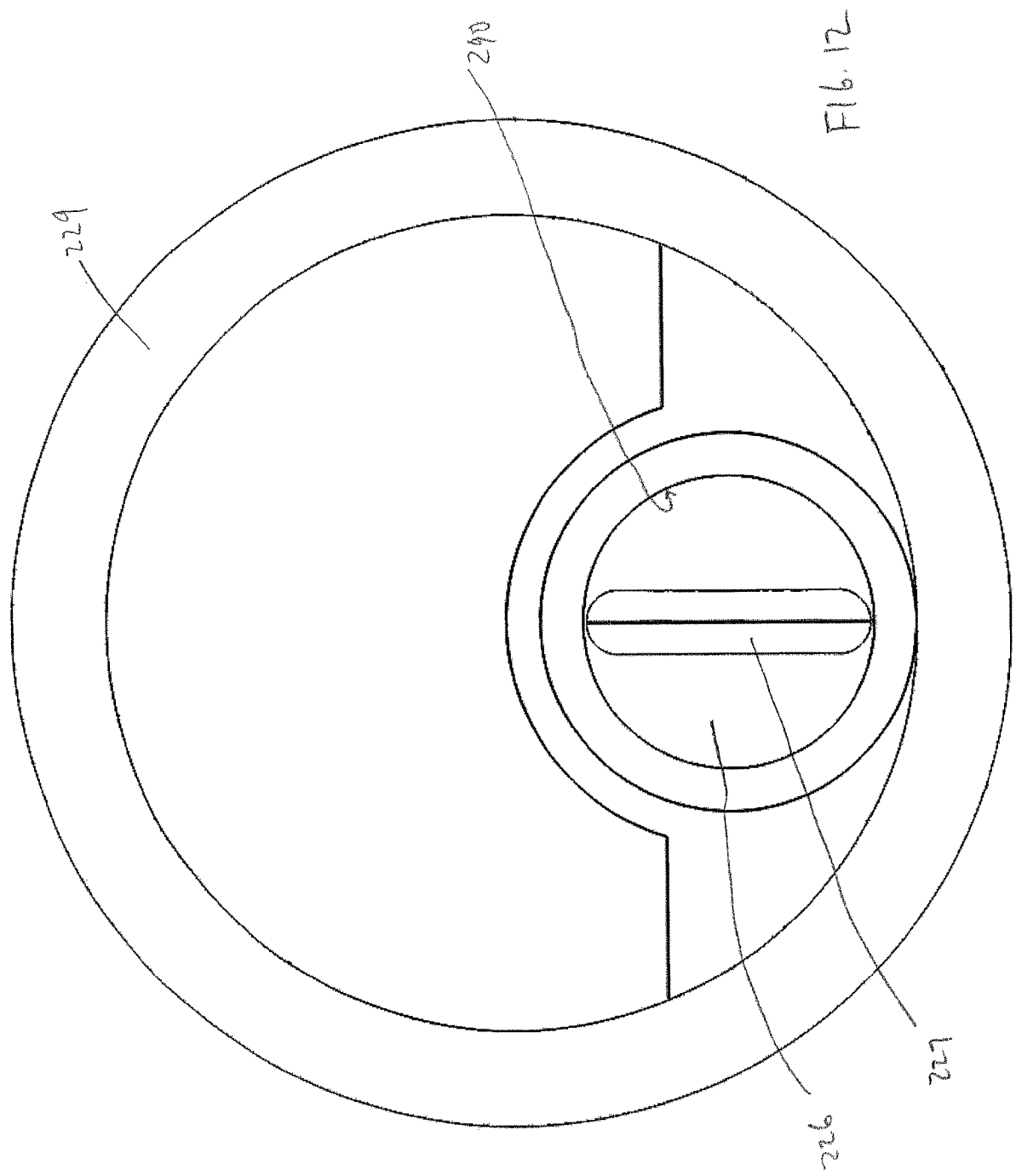
FIG. 12 is a front elevational view of the tube and electrode of the device of FIG. 9.

Turning to FIG. 12, a channel is formed in the blade holder 233 for receiving the electrode 226. The surgical smoke is evacuated through the passageway formed around the blade holder 233. An opening 290 formed in the blade holder 233 mounted in the tube 229 is sized to receive one or more electrodes 226. The opening 290 leads to a channel extending axially along the length of the tube 229. At the end of the channel 233 the base 230 of the electrode 226 contacts the conductor 256 to establish electrical contact between the electrode 226 and the electrical circuit in the device 220. The electrical circuit in the device 220 provides current to the electrode 226. The current may be provided at different levels depending on the application. For cutting, a higher current level is required, whereas, coagulation requires less current.

Figure 13:
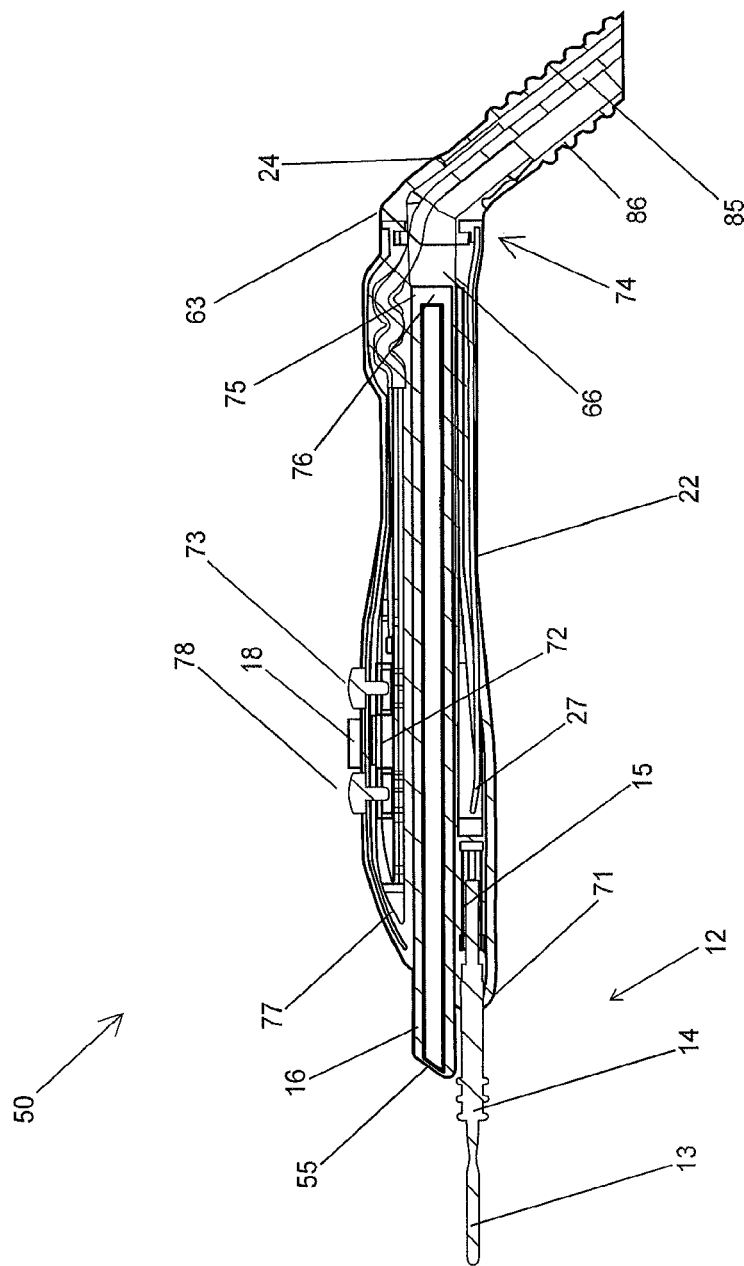
FIG. 13 is a section view of a second embodiment of an electrosurgical device.

In FIG. 13, the electrosurgical device is shown as broadly including hollow body 22 with a front end holding electrode 12, a rear end holding vacuum port 24, electrical line 85, coagulate/coagulate rocker switch 18, and vacuum 16. Vacuum tube 16 is slidably engaged by hollow body 22 and is shown in the retracted configuration in FIG. 13.

Electrode 12 has uninsulated portion 13, connected to insulated portion 14. As shown in FIG. 13, insulated portion 14 contains circular ridges. Connected to insulated portion 14 is uninsulated portion 15 which is reversibly and compressively engaged by hollow body 22. When engaged by hollow body 22, electrode 12 makes electrical contact with internal wire 27 which is connected to electrical line 85 through rocker switch 18 within elongated body 22. Also, when electrode 12 is engaged to body 22, portion 14 of electrode 12 extends out of body 22 and can be easily gripped by a user's fingers.

Figure 14:
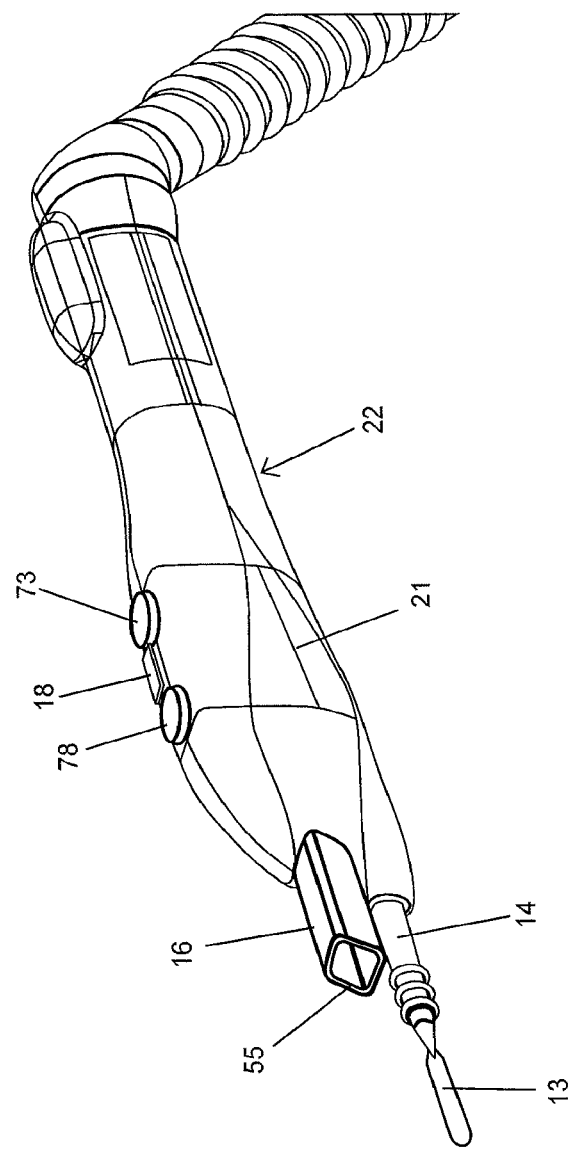
FIG. 14 is a perspective view of the second embodiment.
Figure 15:
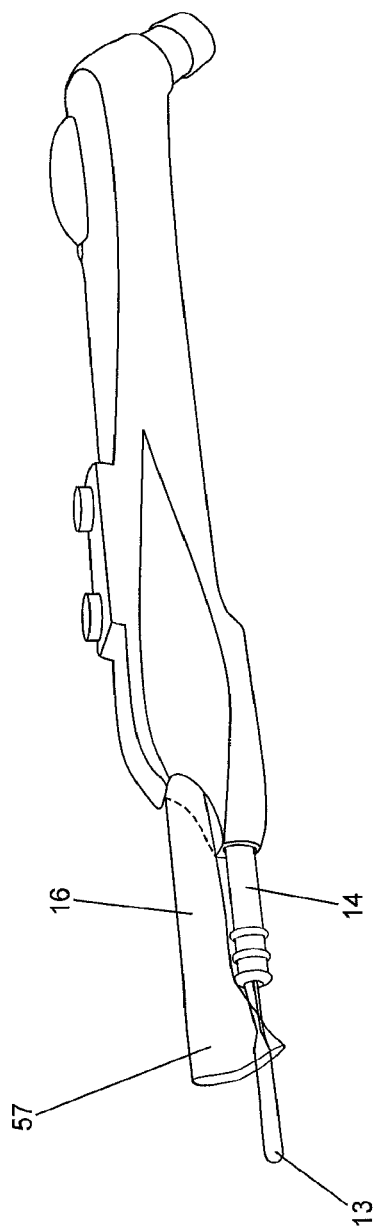
FIG. 15 is a side view of a third embodiment with a flared vacuum tube inlet.
Figure 16:
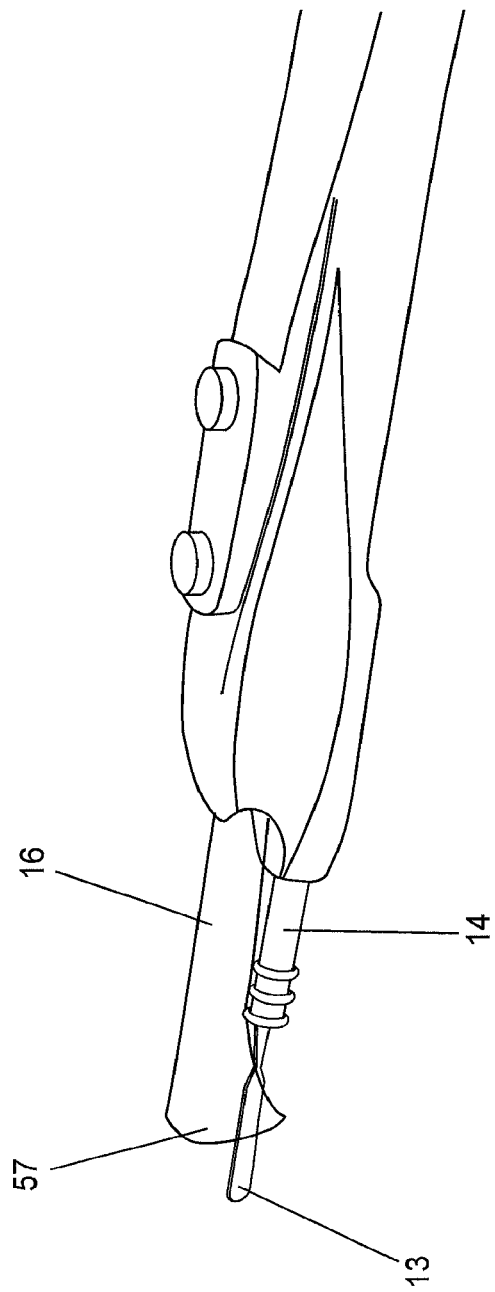
FIG. 16 is a perspective view of the third embodiment with a flared vacuum tube inlet.
Figure 17:
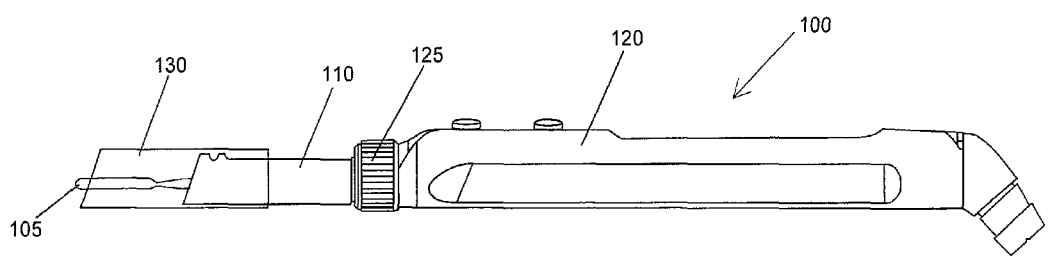
FIG. 17 is a side view of a fourth embodiment having a retractable electrode mount and a vacuum tube which surrounds the electrode mount.
Figure 18:
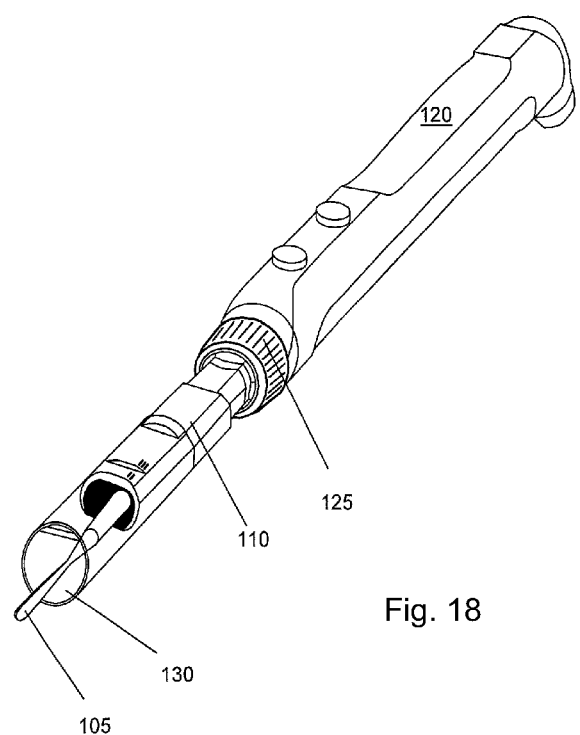
FIG. 18 is a perspective view of the fourth embodiment.
Figure 19A:
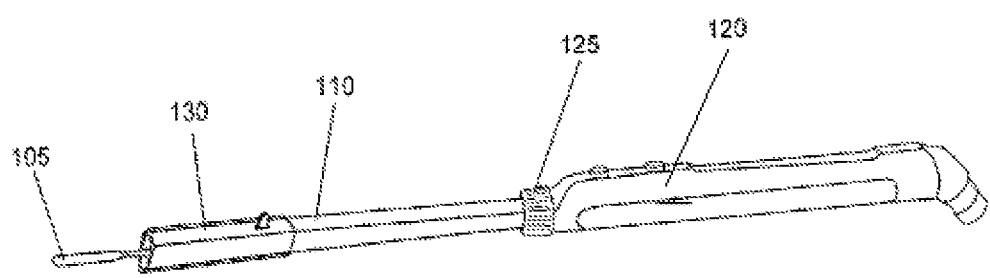
FIGS. 19a and 19b are side view of the fourth embodiment in retracted and extended configurations.
Figure 19B:
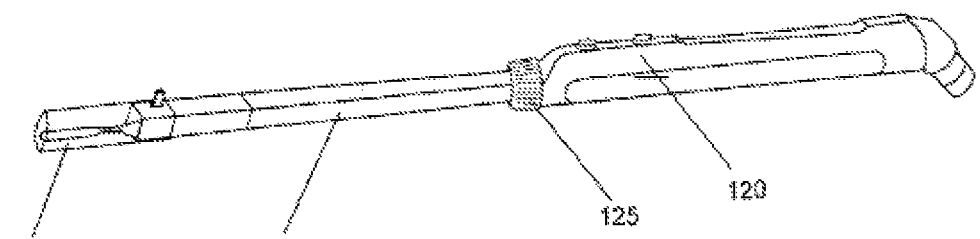
Figure 20A:
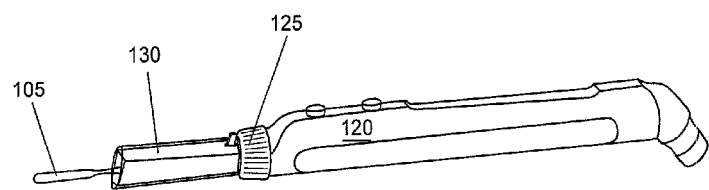
FIGS. 20a and 20b are side views of the fourth embodiment in retracted and extended configurations.
Figure 20B:
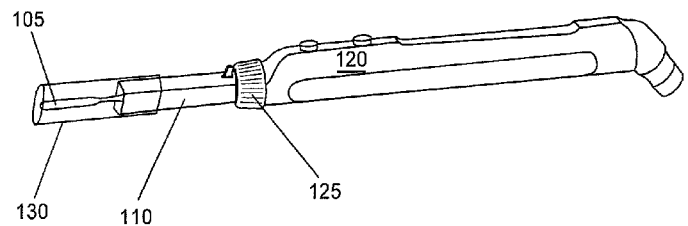
Figure 21:
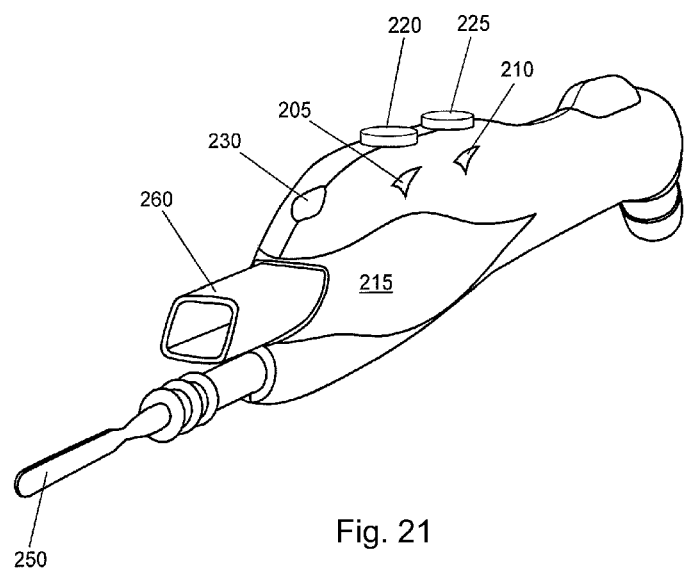
FIG. 21 is a side view of a fifth embodiment with indicated lights for the buttons.
Figure 22:
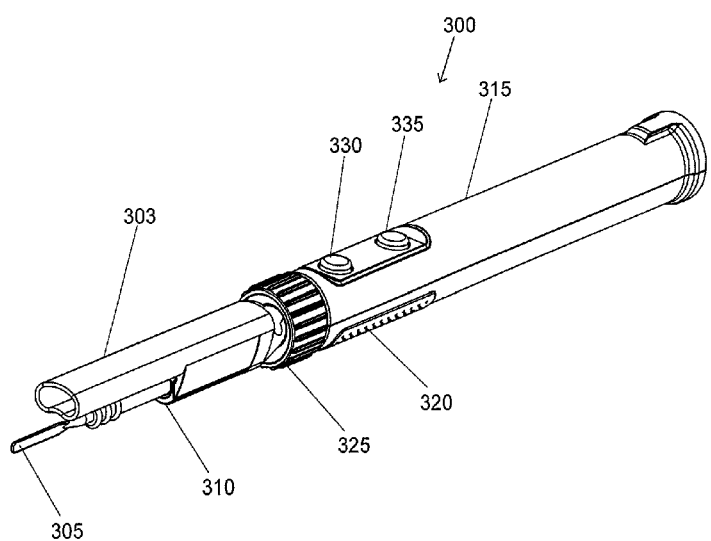
FIG. 22 is a perspective view of the fifth embodiment.
Figure 23:
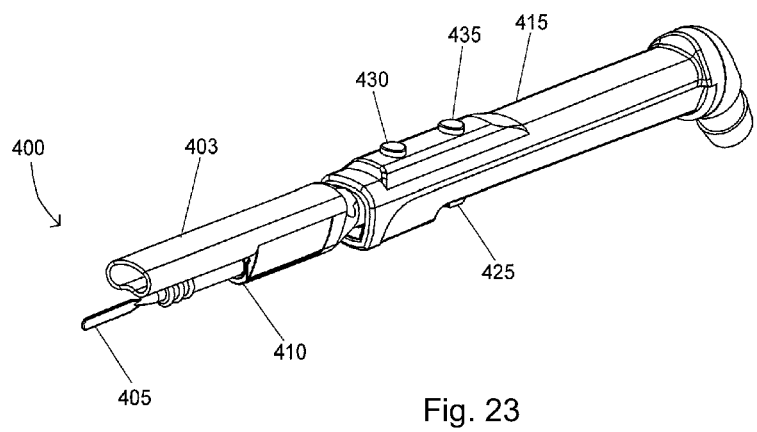
FIG. 23 is a perspective view of the fifth embodiment.
Figure 24:
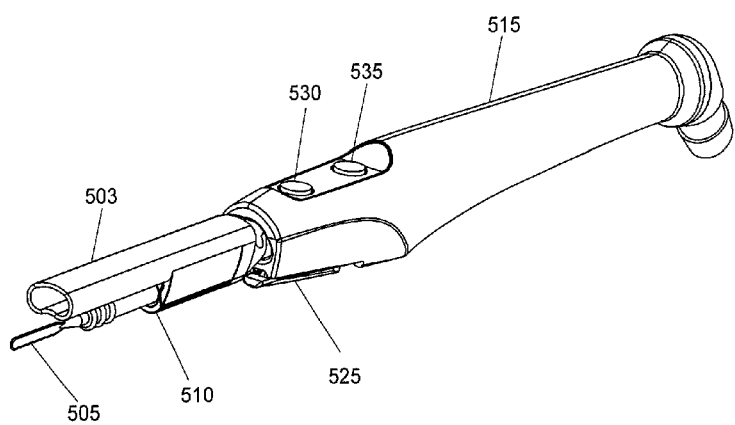
FIG. 24 is an alternative embodiment including alternate locking mechanisms.
Figure 25:
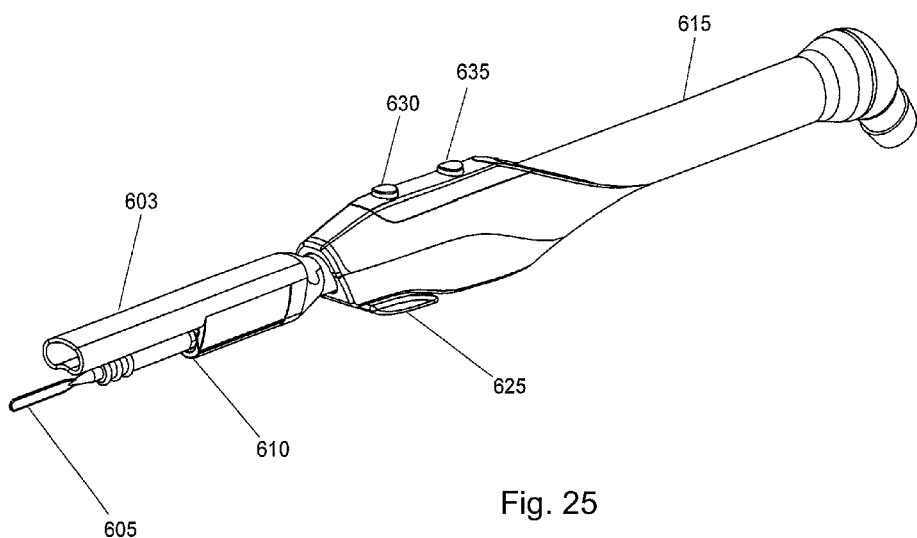
FIG. 25 is an alternative embodiment.
Figure 26:
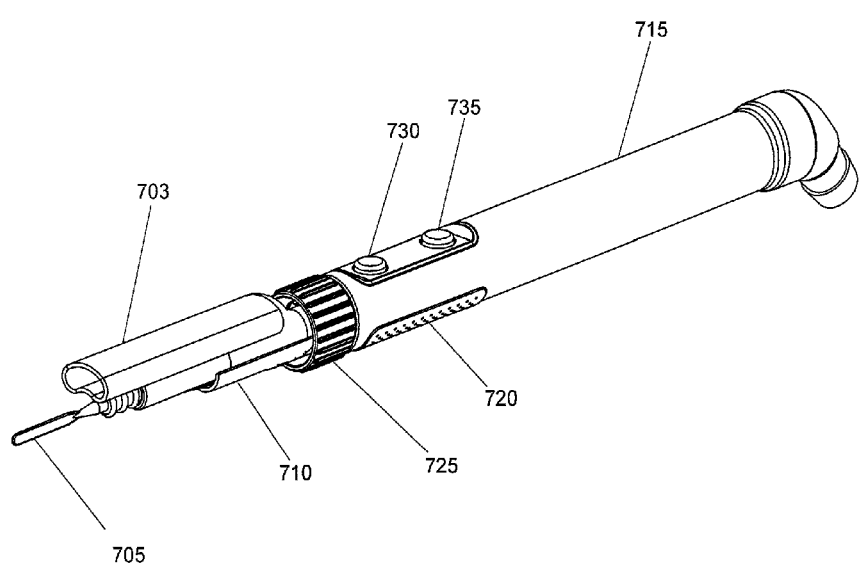
FIG. 26 is a perspective view of another alternative embodiment.
Figure 27:
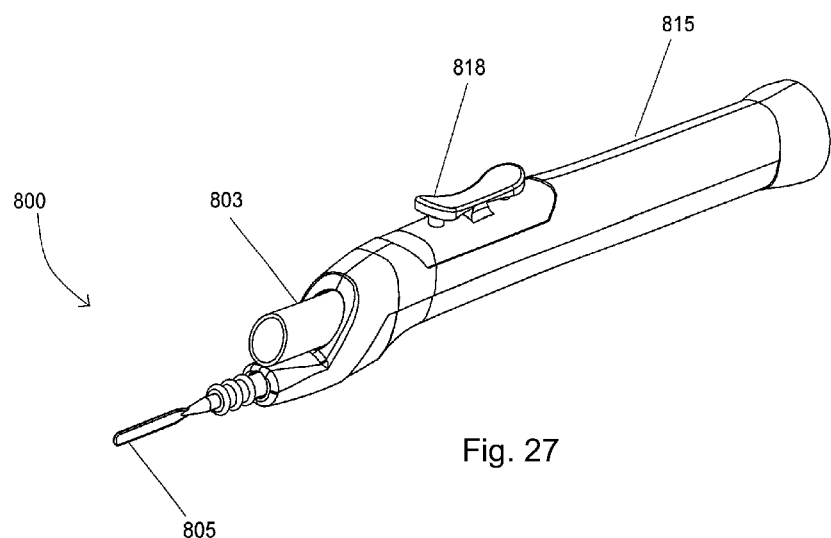
FIG. 27 is a perspective view of yet another alternative embodiment.

FIGS. 13 and 14 show second embodiment with vacuum tube 16 in the retracted configuration. In the extended configuration, inlet 55 is positioned closer to electrode portion 13.

A user first prepares second embodiment 55 by inserting electrode 12 into the front end of elongated body 22. By holding electrode 12 by its insulated portion 14, the circular ridges along insulated portion 14 provide increased friction and grip for inserting electrode 12 into body 22. Electrode 12 is firmly pressed into body 22 such electrode 12 makes electrical contact with internal wire 27 within body 22. Since insulated portion 14 extends outside body 22 when electrode 12 is fully inserted, the user is able to insert the electrode without ever touching uninsulated portion 13 of electrode 12.

The user next adjusts vacuum tube 16 to the proper extension distance. The lateral edges of vacuum tube 16 are not hindered by body 22 and the user can easily grip vacuum tube 16 by the lateral edges and telescopically adjust the vacuum tube to an appropriate extension amount.

An external vacuum tube is connected to outlet port 24 is securely inserted such that an air-tight seal is formed. The opposing end of the external vacuum tube is connected to a vacuum source, and electrical line 85 is connected to an electrosurgical FR power source.

In preparation for electrosurgery, the user will grip body 22 similar to holding a pencil, and the user's thumb and non-index fingers will be placed on opposite sides of body 22 along finger friction texture 21. As shown in FIG. 14, the shape of the device is ergonometrically suited to a user's hand. When the user is ready to initiate electrosurgery, the vacuum source will be toggled on by pressing vacuum control button 73. If illumination is desired, toggle button 78 is pressed to turn on illumination light 71. Rocker switch 18 will next be pressed either forwards or backwards with a user's index finger to cause wither a cutting or a coagulation mode to be initiated. Pressing button 18 will cause current to pass from electrical line 85 to internal wire 27 and out electrode 12 to a patient's body. The electrical current through the tissue causes intense heat and smoke, typically causing cutting or coagulation of tissue.

Smoke produced during electrosurgery is suctioned by vacuum tube 16. During surgery, the user may easily adjust vacuum tube 16's position, either extending it closer to electrode portion 13 in order better capture smoke, or retracting it closer towards body 22 in order to provide the user with a less obstructed view of the surgical area. The average current level for coagulate will be less than for cutting.

Since vacuum tube 16 is arranged above electrode portion 13, it is in a good position to capture smoke which typically travels upwards from the treatment region. In this position above the electrode, vacuum tube 16 is more likely to capture smoke than if it were arranged under electrode 13. Additionally, since vacuum tube is not on the bottom side of body 22, there is decreased risk of vacuum inlet 15 coming into contact with the patient's body which could cause trauma.

During the surgery, whenever the user's hand rotates along the elongated body's longitudinal axis, the swivel between bend 23 and outlet port 24 allows torsional strain to be released. If during the surgery a different electrode style is needed, the user may easily pull electrode 12 off of body 22. Since insulated portion 14 of electrode 12 is easily accessible to the user's fingers, the user may easily remove electrode 12 without touching electrically uninsulated areas of the electrode. This is an added safety feature to help prevent the user from being burned from unanticipated activation of the electrosurgical device. The circular friction ridges along insulated portion 14 and friction texture 21 along elongated body 22 also help to provide increased stability during the process of removing and inserting electrodes.

Since electric line 85 passes through vacuum port 24, it will not wrap around the external vacuum tube when the electrosurgical device is twisted relative to the external vacuum tube. This reduces the chance of discomfort for the user by preventing rotational strains on the user's movement.

As shown, vacuum inlet 55 is angled such that when the device is held correctly during surgery, the cross section of the nozzle will be substantially parallel to the user's line of sight as the user looks at the treatment area. In this arrangement, vacuum inlet 55 can be placed as close as possible to the treatment area. In this arrangement, vacuum inlet 55 can be placed as close as possible to the treatment area without obstructing the user's view. For example, in this configuration, both the top of the nozzle and the bottom of the nozzle are right up flush with the user's line of sight, as close as possible to the smoke creation region before starting to obstruct the user's view.

Additionally, as shown in FIG. 13, vacuum tube 16 has a rectangular shaped cross section. While the rectangular cross section allows for the complete electrosurgical device to have a shorter vertical profile, a crescent shaped cross section in alternative embodiments allows the vacuum tube to more closely enclose the electrode to increase the chances of more completely sucking up the created smoke. The shorter vertical profile makes the electrosurgical device easier to handle.

The embodiments disclosed resulted in a number of unexpected results. By arranging the vacuum tubes above the electrode instead of below the electrode a greater portion of the smoke plume was able to be captured. Additionally, by no longer having the vacuum tube on the bottom of the electrosurgical device, the chances of injuring the patient from trauma cause by accidentally bringing the vacuum inlet nozzle onto the patient's exposed surgical site is reduced.

The user's view of the surgical site was surprisingly greatly improved by using a clear vacuum tube. Since light can easily pass through the vacuum tube, reduced amount of shadows are cast on the surgical site. Additionally, since the vacuum tube level of extension can be telescopically adjusted, an optical configuration is obtained for user's of different heights or styles of holding the electrosurgical device. Further, since not all electrodes are the same length, the vacuum tube extension can be adjusted to match the particular electrode used. The upward angled configuration of the vacuum inlet is also particularly advantageous in that it allows the suction source to get as close to the smoke generation region as possible without obstructing the user's view.

By designing the electrosurgical device such that an insulated portion of the electrode is available to be grabbed when the electrode is fully inserted, the insertion and removal of electrodes is made easier and safe. The user is less likely to get accidently burned when changing the electrode since he/she can grid the electrode on an electrically insulated portion. Further, the use of friction ridges on the insulated portion of the electrode and the elongated body sides, the chance that the device slips in the user's hands is reduced. This is particularly important since the surgical process is likely to cause blood and other slippery body fluids to end up on the device.

The disclosed embodiments also increase surgical efficiency through the illumination offered by an attached light, the reduction of rotational strain by the external vacuum tube swivel and electrical line positioning within the swivel, and the button for controlling the vacuum source. Additionally, the RF sensor within the electrosurgical device allows the vacuum source to be automatically controlled by a circuit which is electrically isolated from the electrosurgical power supply.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

The invention claimed is:

1. An electrosurgical device comprising:
   an electrode having a first portion whose exterior is electrically uninsulated, a second portion whose exterior is electrically insulated, and a third portion;
   an elongated hollow body having an internal cavity, a front end, a rear end, an external surface, and an electrical circuit arranged within said body;
   a first button for controlling a current flow at a first level to said electrode and arranged on said external surface;
   a second button for controlling a current flow at a second level to said electrode and arranged on said external surface; and
   a vacuum tube slidably engaged by said body and having an inlet generally facing said front end, said vacuum tube circumscribing said electrode such said first portion of said electrode is not surrounded by said vacuum tube, wherein the vacuum tube comprises an inlet shaped to have a cross section that is generally circular shaped, wherein said vacuum tube comprises a pair of spaced apart lips extending radially inward from an interior surface of the vacuum tube and a blade holder mounted inside said vacuum tube such that said blade holder is located approximately inside a center of said vacuum tube, said blade holder comprising a conductor that is electrically connected to said electrical circuit and said electrode, said blade holder and a portion of said conductor is located in a portion of said vacuum tube that extends outside the elongated hollow body, said blade holder comprising (i) a longitudinal channel operable for receiving said electrode, and (ii) a pair of spaced apart radial extending ribs that are in contact with an interior surface of said vacuum tube and maintained in place by the spaced apart lips, wherein said blade holder is spaced from said interior surface of said vacuum tube, wherein the blade holder, the pair of spaced apart radial extending ribs and an interior surface of the vacuum tube are operably spaced from one another to allow a flow of fluid therebetween;
a vacuum outlet port arranged near said rear end, said outlet port, internal cavity, and inlet in fluid communication with each other; and
a swivel joint disposed between said hollow body and said outlet port.

2. An electrosurgical device as set forth in claim 1 wherein said body is ergonometrically shaped to be received by a user's hand.

3. An electrosurgical device as set forth in claim 1 wherein said body is pencil shaped.

4. An electrosurgical device as set forth in claim 1 wherein said body contains friction striations.

5. An electrosurgical device as set forth in claim 1 wherein said electrode is monopolar, bipolar, or sesquipolar.

6. An electrosurgical device as set forth in claim 1, wherein the vacuum tube comprises an inlet shaped to have a cross section generally vertical relative to a long axis of the hollow body and the electrode.

7. An electrosurgical device as set forth in claim 1 and further comprising:
a light source arranged to illuminate an area near said electrode;
a battery for providing power to said light source; and
a button for controlling said light source.

8. An electrosurgical device as set forth in claim 1 and further comprising a filter arranged within said internal cavity.

9. An electrosurgical device as set forth in claim 8 wherein said filter comprises an RFID tag containing filter information.

10. An electrosurgical device comprising:
an electrode;
an elongated hollow body having an internal cavity, a front end, a rear end, an external surface, and an electrical circuit arranged within said body;
said hollow body shaped to have an ergonometric orientation complementary to a user's hand;
a first button for controlling a current flow at a first level to said electrode and arranged on said external surface; and,
a vacuum tube slidably engaged by said body and having an inlet, said vacuum tube circumscribing said electrode such that a second portion of said electrode is not surrounded by said vacuum tube, wherein the vacuum tube comprises an inlet shaped to have a cross section parallel to a user's line of sight towards said electrode when using said device, wherein said vacuum tube comprises a pair of spaced apart lips extending radially inward from an interior surface of the vacuum tube and a blade holder mounted inside said vacuum tube such that said blade holder is located approximately inside a center of said vacuum tube, said blade holder comprising a conductor that is electrically connected to said electrical circuit and said electrode, said blade holder and a portion of said conductor is located in a portion of said vacuum tube that extends outside the elongated hollow body, said blade holder comprising (i) a longitudinal channel operable for receiving said electrode, and (ii) a pair of spaced apart radial extending ribs that are in contact with an interior surface of said vacuum tube and maintained in place by the spaced apart lips, wherein said blade holder is spaced from said interior surface of said vacuum tube, wherein the blade holder, the pair of spaced apart radial extending ribs and an interior surface of the vacuum tube are operable space from one another to allow a flow of fluid therebetween;
a vacuum outlet port arranged near said rear end, said outlet port, internal cavity, and inlet in fluid communication with each other; and
a swivel joint disposed between said hollow body and said outlet port.

11. An electrosurgical device as set forth in claim 10 wherein said electrode is configured to have an electrically insulated portion not surrounded by said elongated hollow body when said electrode is received by said blade holder.

12. An electrosurgical device as set forth in claim 10 wherein said body is pencil shaped.

13. An electrosurgical device as set forth in claim 10 wherein said body contains curved friction striations.

14. An electrosurgical device as set forth in claim 10 wherein said electrode is monopolar, bipolar, or sesquipolar.

15. An electrosurgical device as set forth in claim 10 and further comprising a second button for controlling a current flow at a second level to said electrode.

16. An electrosurgical device comprising:
an electrode having a first portion whose exterior is electrically uninsulated;
an elongated hollow body having an internal cavity, a front end, a rear end, an external surface, and an electrical wire arranged within said body;
said hollow body shaped to have an ergonometric orientation complementary to a user's hand;
a first button for controlling a current flow at a first level to said electrode and arranged on said external surface;
a vacuum tube engaged by said body and having an inlet generally facing said front end, said vacuum tube surrounding said electrode, wherein said vacuum tube comprises a pair of spaced apart lips extending radially inward from an interior surface of the vacuum tube and a blade holder mounted inside said vacuum tube such that said blade holder is located approximately inside a center of said vacuum tube, said blade holder comprising a conductor that is electrically connected to said electrical circuit and said electrode, said blade holder and a portion of said conductor is located in a portion of said vacuum tube that extends outside the elongated hollow body, said blade holder comprising (i) a longitudinal channel operable for receiving said electrode, and (ii) a pair of spaced apart radial extending ribs that are in contact with an interior surface of said vacuum tube and maintained in place by the spaced apart lips, wherein said blade holder is spaced from said interior surface of said vacuum tube, wherein the blade holder, the pair of spaced apart radial extending ribs and an interior surface of the vacuum tube are operable space from one another to allow a flow of fluid therebetween;
a vacuum outlet port arranged near said rear end, said outlet port, internal cavity, and vacuum inlet in fluid communication with each other;
wherein said vacuum tube is positioned such that it does not obstruct a user's view of said electrode during use, wherein said vacuum tube comprises the inlet to the vacuum tube being shaped to have a cross section parallel to a user's line of sight towards said electrode when using said device.

17. An electrosurgical device as set forth in claim 16 wherein said electrode comprises an insulation coating on said electrode which remains accessible to a user's hand when said electrode is received by said body.

18. An electrosurgical device as set forth in claim 16, wherein the inlet of the vacuum tube is shaped to have a cross-section disposed at an acute angle with respect to a longitudinal axis of the electrosurgical device.

\* \* \* \* \*